United States Patent [19]

Hatanaka et al.

[11] Patent Number: 5,674,906

[45] Date of Patent: Oct. 7, 1997

[54] STILBENE COMPOUNDS AND PHARMACEUTICAL COMPOSITIONS CONTAINING THEM

[75] Inventors: Toshihiro Hatanaka; Koji Ohsumi; Takashi Tsuji; Yukio Nihei; Ryusuke Nakagawa; Kazuo Ohishi, all of Kawasaki, Japan

[73] Assignee: Ajinomoto Co., Inc., Tokyo, Japan

[21] Appl. No.: 612,416

[22] Filed: Mar. 7, 1996

[30] Foreign Application Priority Data

Mar. 7, 1995 [JP] Japan ................. 7-047581

[51] Int. Cl.$^6$ ................. A61K 31/16; A61K 31/195; A61K 31/275; A61K 31/40
[52] U.S. Cl. ................. 514/626; 514/419; 514/423; 514/521; 514/563; 514/620; 548/491; 548/537; 558/402; 562/450; 564/194
[58] Field of Search ................. 514/419, 423, 514/521, 563, 620, 626; 548/491, 537; 558/402; 562/450; 564/194

[56] References Cited

U.S. PATENT DOCUMENTS 3,246,983  4/1966  Sus et al. ................. 96/1

FOREIGN PATENT DOCUMENTS

| 0 641 767 | 3/1995 | European Pat. Off. . | |
|---|---|---|---|
| 06316543 | 11/1994 | Japan | 558/402 |
| WO-A-93 23357 | 11/1993 | WIPO . | |

*Primary Examiner*—Peter O'Sullivan
*Attorney, Agent, or Firm*—Sughrue, Mion, Zinn, Macpeak & Seas, PLLC

[57]  ABSTRACT

Stilbene compounds of the following formula (I) or their pharmaceutically acceptable salts are effective as carcinostatics and of low toxicity:

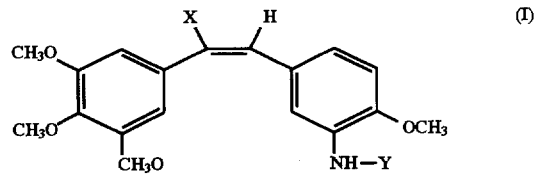

(I)

wherein X represents a hydrogen atom or a nitrile group, and Y represents an amino acid acyl group.

7 Claims, No Drawings

STILBENE COMPOUNDS AND PHARMACEUTICAL COMPOSITIONS CONTAINING THEM

FIELD OF THE INVENTION

The present invention relates to cis-stilbene compounds, to their use as pharmaceuticals and, in particular, to carcinostatics containing them as active ingredients.

BACKGROUND OF THE INVENTION

It is known that combretastatins with cis-stilbene as their basic skeleton have strong mitosis inhibitory activity and strong cytotoxicity. However, since these compounds are barely soluble in water, they have not been put to practical use as medicines. Therefore, derivatives thereof have been studied (*Molecular Pharmacology* 34, Chii M. Lin et al., 200–206, 1988, *J. Med. Chem.*, Mark Cushman et al., 1991, 34, 2579–2588, International Laid-Open Patent Application WO 92/16486, *J. Med. Chem.*, Marck Cushman et al., 1992, 35, 2293–2306, International Laid-Open Patent Application WO 93/23357, *J. Med. Chem.*, Mark Cushman et al., 1993, 36, 2817–2821, and *Bioorg. Med. Chem. Let.*, Ryuichi Shirai et al., vol. 4, No. 5, pp. 699–704, 1994). Nevertheless, effective compounds have not yet been discovered.

SUMMARY OF THE INVENTION

The present invention relates to combretastatin compounds which can be easily synthesized, which have low toxicity and which have carcinostatic pharmaceutical effects, and to provide carcinostatics containing them.

The present inventors have studied various stilbene compounds which have an amino acid acyl group and screened carcinostatic compounds from them. Consequently, they have found that compounds of the following formula (I) have a remarkable carcionstatic effect and low toxicity when tested in standard animal tests.

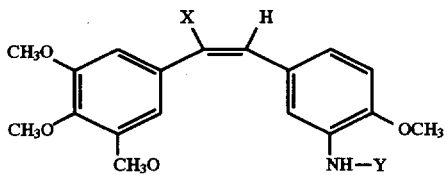

(I)

wherein X represents a hydrogen atom or a nitrile group, and Y represents an amino acid acyl group.

DETAILED DESCRIPTION OF THE INVENTION

In formula (I), the amino acid acyl group is an acyl group derived from an amino acid. Suitable amino acids include α-amino acids, β-amino acids and γ-amino acids. Preferable examples of the amino acid include glycine, alanine, leucine, serine, lysine, glutamic acid, aspartic acid, threonine, valine, isoleucine, ornithine, glutamine, asparagine, tyrosine, phenylalanine, cysteine, methionine, arginine, β-alanine, tryptophan, proline, and histidine. Threonine and serine are especially preferred in terms of pharmaceutical effects and safety. These amino acids may be used as L-isomers or D-isomers or a racemic mixture can be employed. L-isomers are preferable.

Preferable examples of the compounds of the formula (I) are as follows:

(Z)-1-(3-amino-4-methoxyphenyl)-2-(3,4,5-trimethoxyphenyl)-ethene-glycineamide (Z)-1-(3-amino-4-methoxyphenyl)-2-(3,4,5-trimethoxyphenyl)-ethene-L-alanineamide (Z)-1-(3-amino-4-methoxyphenyl)-2-(3,4,5-trimethoxyphenyl)-ethene-β-alanineamide (Z)-1-(3-amino-4-methoxyphenyl)-2-(3,4,5-trimethoxyphenyl)-ethene-L-leucineamide (Z)-1-(3-amino-4-methoxyphenyl)-2-(3,4,5-trimethoxyphenyl)-ethene-L-serineamide (Z)-1-(3-amino-4-methoxyphenyl)-2-(3,4,5-trimethoxyphenyl)-ethene-L-threonineamide (Z)-1-(3-amino-4-methoxyphenyl)-2-(3,4,5-trimethoxyphenyl)-ethene-L-valineamide (Z)-1-(3-amino-4-methoxyphenyl)-2-(3,4,5-trimethoxyphenyl)-ethene-L-isoleucineamide (Z)-1-(3-amino-4-methoxyphenyl)-2-(3,4,5-trimethoxyphenyl)-ethene-L-prolineamide (Z)-1-(3-amino-4-methoxyphenyl)-2-(3,4,5-trimethoxyphenyl)-ethene-L-methionineamide (Z)-1-(3-amino-4-methoxyphenyl)-2-(3,4,5-trimethoxyphenyl)-ethene-L-glutamineamide (Z)-1-(3-amino-4-methoxyphenyl)-2-(3,4,5-trimethoxyphenyl)-ethene-L-glutamylamide (Z)-1-(3-amino-4-methoxyphenyl)-2-(3,4,5-trimethoxyphenyl)-ethene-L-aspartylamide (Z)-1-(3-amino-4-methoxyphenyl)-2-(3,4,5-trimethoxyphenyl)-ethene-L-asparagineamide (Z)-1-(3-amino-4-methoxyphenyl)-2-(3,4,5-trimethoxyphenyl)-ethene-L-lysineamide (Z)-1-(3-amino-4-methoxyphenyl)-2-(3,4,5-trimethoxyphenyl)-ethene-L-histidineamide (Z)-1-(3-amino-4-methoxyphenyl)-2-(3,4,5-trimethoxyphenyl)-ethene-L-arginineamide (Z)-1-(3-amino-4-methoxyphenyl)-2-(3,4,5-trimethoxyphenyl)-ethene-L-cysteineamide (Z)-1-(3-amino-4-methoxyphenyl)-2-(3,4,5-trimethoxyphenyl)-ethene-L-tryptophanamide (Z)-1-(3-amino-4-methoxyphenyl)-2-(3,4,5-trimethoxyphenyl)-ethene-D-alanineamide (Z)-1-(3-amino-4-methoxyphenyl)-2-(3,4,5-trimethoxyphenyl)-ethene-D-leucineamide (Z)-1-(3-amino-4-methoxyphenyl)-2-(3,4,5-trimethoxyphenyl)-ethene-D-serineamide (Z)-1-(3-amino-4-methoxyphenyl)-2-(3,4,5-trimethoxyphenyl)-ethene-D-threonineamide (Z)-1-(3-amino-4-methoxyphenyl)-2-(3,4,5-trimethoxyphenyl)-ethene-D-valineamide (Z)-1-(3-amino-4-methoxyphenyl)-2-(3,4,5-trimethoxyphenyl)-ethene-D-isoleucineamide (Z)-1-(3-amino-4-methoxyphenyl)-2-(3,4,5-trimethoxyphenyl)-ethene-D-prolineamide (Z)-1-(3-amino-4-methoxyphenyl)-2-(3,4,5-trimethoxyphenyl)-ethene-D-glutamineamide (Z)-1-(3-amino-4-methoxyphenyl)-2-(3,4,5-trimethoxyphenyl)-ethene-D-glutamylamide (Z)-1-(3-amino-4-methoxyphenyl)-2-(3,4,5-trimethoxyphenyl)-ethene-D-aspartylamide (Z)-1-(3-amino-4-methoxyphenyl)-2-(3,4,5-trimethoxyphenyl)-ethene-D-asparagineamide (Z)-1-(3-amino-4-methoxyphenyl)-2-(3,4,5-trimethoxyphenyl)-ethene-D-lysineamide (Z)-1-(3-amino-4-methoxyphenyl)-2-(3,4,5-trimethoxyphenyl)-ethene-D-histidineamide (Z)-1-(3-amino-4-methoxyphenyl)-2-(3,4,5-trimethoxyphenyl)-ethene-D-arginineamide (Z)-1-(3-amino-4-methoxyphenyl)-2-(3,4,5-trimethoxyphenyl)-ethene-D-cysteineamide (Z)-1-(3-amino-4-methoxyphenyl)-2-(3,4,5-trimethoxyphenyl)-ethene-D-methionineamide (Z)-1-(3-amino-4-methoxyphenyl)-2-(3,4,5-trimethoxyphenyl)-ethene-D-tryptophanamide
(E)-3-(3-amino-4-methoxyphenyl)-2-(3,4,5-trimethoxyphenyl)prop-2-enenitrile-glycineamide
(E)-3-(3-amino-4-methoxyphenyl)-2-(3,4,5-trimethoxyphenyl)prop-2-enenitrile-L-alanineamide
(E)-3-(3-amino-4-methoxyphenyl)-2-(3,4,5-trimethoxyphenyl)prop-2-enenitrile-β-alanineamide
(E)-3-(3-amino-4-methoxyphenyl)-2-(3,4,5-trimethoxyphenyl)prop-2-enenitrile-L-leucineamide
(E)-3-(3-amino-4-methoxyphenyl)-2-(3,4,5-trimethoxyphenyl)prop-2-enenitrile-L-isoleucineamide
(E)-3-(3-amino-4-methoxyphenyl)-2-(3,4,5-trimethoxyphenyl)prop-2-enenitrile-L-serineamide
(E)-3-(3-amino-4-methoxyphenyl)-2-(3,4,5-trimethoxyphenyl)prop-2-enenitrile-L-threonineamide
(E)-3-(3-amino-4-methoxyphenyl)-2-(3,4,5-trimethoxyphenyl)prop-2-enenitrile-L-phenylaranineamide
(E)-3-(3-amino-4-methoxyphenyl)-2-(3,4,5-trimethoxyphenyl)prop-2-enenitrile-L-tyrosineamide
(E)-3-(3-amino-4-methoxyphenyl)-2-(3,4,5-trimethoxyphenyl)prop-2-enenitrile-L-prolineamide
(E)-3-(3-amino-4-methoxyphenyl)-2-(3,4,5-trimethoxyphenyl)prop-2-enenitrile-L-lysineamide
(E)-3-(3-amino-4-methoxyphenyl)-2-(3,4,5-trimethoxyphenyl)prop-2-enenitrile-L-histidineamide
(E)-3-(3-amino-4-methoxyphenyl)-2-(3,4,5-trimethoxyphenyl)prop-2-enenitrile-L-arginineamide
(E)-3-(3-amino-4-methoxyphenyl)-2-(3,4,5-trimethoxyphenyl)prop-2-enenitrile-L-cysteineamide
(E)-3-(3-amino-4-methoxyphenyl)-2-(3,4,5-trimethoxyphenyl)prop-2-enenitrile-L-methionineamide
(E)-3-(3-amino-4-methoxyphenyl)-2-(3,4,5-trimethoxyphenyl)prop-2-enenitrile-L-tryptophanamide
(E)-3-(3-amino-4-methoxyphenyl)-2-(3,4,5-trimethoxyphenyl)prop-2-enenitrile-L-α-aspartylamide
(E)-3-(3-amino-4-methoxyphenyl)-2-(3,4,5-trimethoxyphenyl)prop-2-enenitrile-L-β-aspartylamide
(E)-3-(3-amino-4-methoxyphenyl)-2-(3,4,5-trimethoxyphenyl)prop-2-enenitrile-L-asparagineamide
(E)-3-(3-amino-4-methoxyphenyl)-2-(3,4,5-trimethoxyphenyl)prop-2-enenitrile-L-α-glutamylamide
(E)-3-(3-amino-4-methoxyphenyl)-2-(3,4,5-trimethoxyphenyl)prop-2-enenitrile-L-γ-glutamylamide
(E)-3-(3-amino-4-methoxyphenyl)-2-(3,4,5-trimethoxyphenyl)prop-2-enenitrile-L-glutamineamide
(E)-3-(3-amino-4-methoxyphenyl)-2-(3,4,5-trimethoxyphenyl)prop-2-enenitrile-D-alanineamide
(E)-3-(3-amino-4-methoxyphenyl)-2-(3,4,5-trimethoxyphenyl)prop-2-enenitrile-D-leucineamide
(E)-3-(3-amino-4-methoxyphenyl)-2-(3,4,5-trimethoxyphenyl)prop-2-enenitrile-D-isoleucineamide
(E)-3-(3-amino-4-methoxyphenyl)-2-(3,4,5-trimethoxyphenyl)prop-2-enenitrile-D-serineamide
(E)-3-(3-amino-4-methoxyphenyl)-2-(3,4,5-trimethoxyphenyl)prop-2-enenitrile-D-threonineamide
(E)-3-(3-amino-4-methoxyphenyl)-2-(3,4,5-trimethoxyphenyl)prop-2-enenitrile-D-phenylaranineamide
(E)-3-(3-amino-4-methoxyphenyl)-2-(3,4,5-trimethoxyphenyl)prop-2-enenitrile-D-tyrosineamide
(E)-3-(3-amino-4-methoxyphenyl)-2-(3,4,5-trimethoxyphenyl)prop-2-enenitrile-D-prolineamide
(E)-3-(3-amino-4-methoxyphenyl)-2-(3,4,5-trimethoxyphenyl)prop-2-enenitrile-D-lysineamide
(E)-3-(3-amino-4-methoxyphenyl)-2-(3,4,5-trimethoxyphenyl)prop-2-enenitrile-D-histidineamide
(E)-3-(3-amino-4-methoxyphenyl)-2-(3,4,5-trimethoxyphenyl)prop-2-enenitrile-D-arginineamide
(E)-3-(3-amino-4-methoxyphenyl)-2-(3,4,5-trimethoxyphenyl)prop-2-enenitrile-D-cysteineamide
(E)-3-(3-amino-4-methoxyphenyl)-2-(3,4,5-trimethoxyphenyl)prop-2-enenitrile-D-methionineamide
(E)-3-(3-amino-4-methoxyphenyl)-2-(3,4,5-trimethoxyphenyl)prop-2-enenitrile-D-tryptophanamide
(E)-3-(3-amino-4-methoxyphenyl)-2-(3,4,5-trimethoxyphenyl)prop-2-enenitrile-D-α-aspartylamide
(E)-3-(3-amino-4-methoxyphenyl)-2-(3,4,5-trimethoxyphenyl)prop-2-enenitrile-D-β-aspartylamide
(E)-3-(3-amino-4-methoxyphenyl)-2-(3,4,5-trimethoxyphenyl)prop-2-enenitrile-D-asparagineamide
(E)-3-(3-amino-4-methoxyphenyl)-2-(3,4,5-trimethoxyphenyl)prop-2-enenitrile-D-α-glutamylamide
(E)-3-(3-amino-4-methoxyphenyl)-2-(3,4,5-trimethoxyphenyl)prop-2-enenitrile-D-γ-glutamylamide
(E)-3-(3-amino-4-methoxyphenyl)-2-(3,4,5-trimethoxyphenyl)prop-2-enenitrile-D-glutamineamide The compound of formula (1) in the present invention can be synthesized by one skilled in the art, for example, according to the reaction schemes shown below.

(A) Where X represents a hydrogen atom

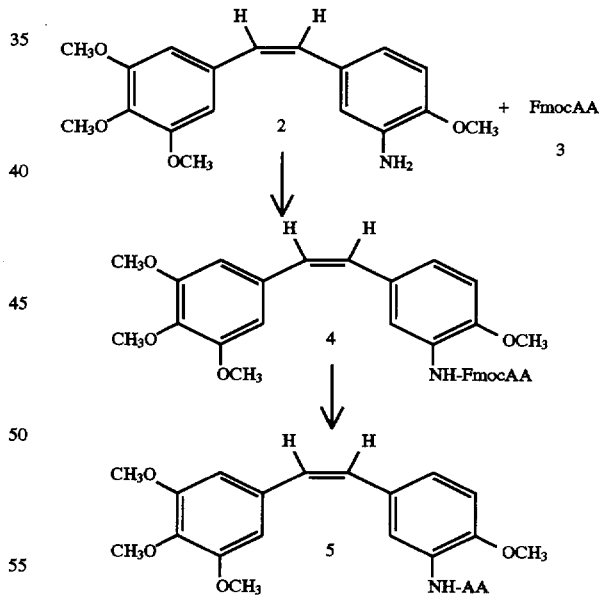

wherein Fmoc represents an N-α-9-fluorenylmethoxycarbonyl group, and AA represents an amino acid acyl group.

(B) Where X represents a nitrile group

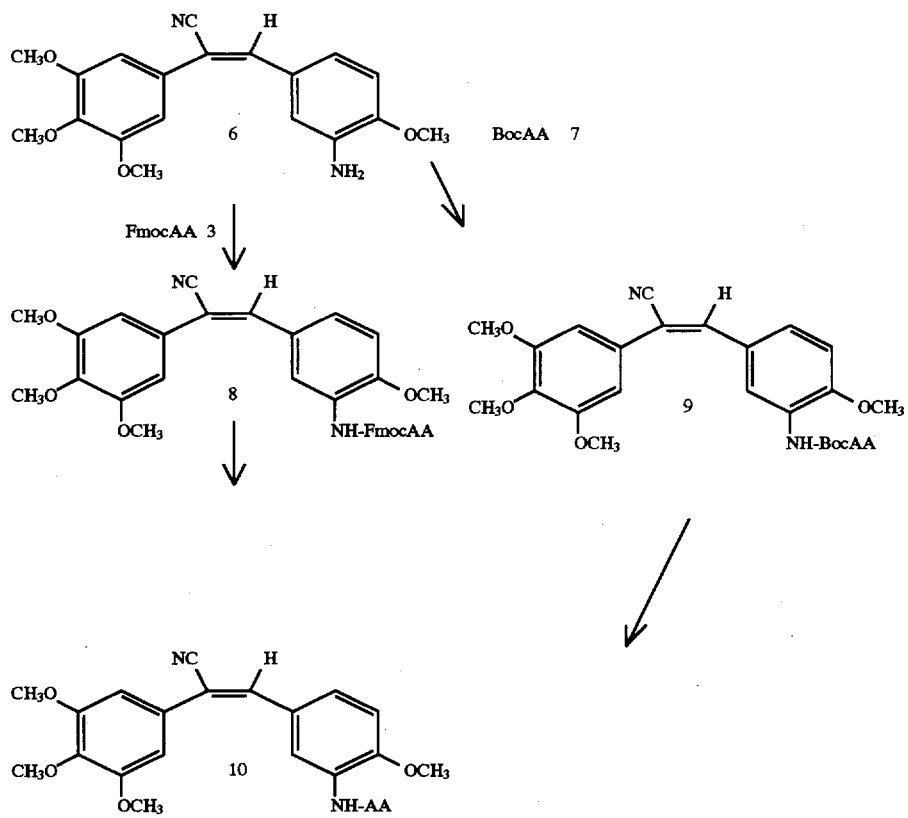

wherein Fmoc and AA are as defined above, and Boc represents a tert-butoxycarbonyl group.

Where X represents a hydrogen atom, the compound of formula (5) in the present invention can be formed by, for example, reacting (Z)-1-(3-amino-4-methoxyphenyl)-2-(3, 4,5-trimethoxyphenyl)-ethene of formula (2) with the N-α-9-fluorenylmethoxycarbonylamino acid compound of formula (3) at room temperature (about 20°–30° C.) for from 6 to 12 hours in dimethylformamide and in the presence of dicyclohexylcarbodiimide (DCC) and 1-hydroxybenzotriazole (HOBt), then purifying the reaction mixture using chromatography or the like to obtain an intermediate (4). This is followed by deprotecting the intermediate (4) with a sodium hydroxide aqueous solution to obtain the compound of the formula (5).

Where X represents a nitrile group, the compound of formula (10) in the present invention can be formed by, for example, reacting (E)-3-(3-amino-4-methoxyphenyl)-2-(3, 4,5-trimethoxyphenyl)-prop-2-enenitrile of formula (6) with the N-α-tert-butoxycarbonylamino acid compound of formula (7) at 50° C. for 4 hours in N,N-dimethylformamide and in the presence of 1-ethyl-3-(3-dimethylaminopropyl) carbodiimide (WSCI) to obtain the compound of formula (9). Then the compound of the formula (9) is deprotected with a mixture of hydrochloric acid and dioxane. Alternatively, the compound of formula (10) can be formed by reacting the compound of formula (6) with the amino acid compound of formula (3) at 60° C. for 24 hours in acetonitrile and in the presence of benzotriazol-1-yl-oxy-tris (dimethylamino)phosphonium hexafluorophosphate (BOP reagent) and triethylamine to form the compound of formula (8). Again, the compound of formula (8) is deprotected with a sodium hydroxide aqueous solution or piperidine.

The stilbene compounds of the present invention which are produced by the above-mentioned processes can be easily separated from the reaction mixture and purified through extraction with a solvent, chromatography, crystallization or the like.

When the above-described stilbene compounds are used as an antitumor agent, the agent can be administered either orally or parenterally (intramuscularly, subcutaneously, intravenously) or in the form of suppositories or the like. The dose of the stilbene compound varies with the degree of progression of the disease. It is usually between 1 and 3,000 mg for an adult per administration. The agent is generally administered in multiple portions in a total amount of from 1 to 9,000 mg/day.

When the stilbene compounds of the present invention are formulated into oral preparations, an excipient, a binder, a disintegrant, a lubricant, a colorant, a corrigent and the like are added thereto as required, and the resulting mixture is formed into tablets, coated tablets, granules, capsules or the like. Examples of suitable excipients include lactose, corn starch, saccharide, dextrose, sorbitol, and crystalline cellulose. Examples of suitable binders include polyvinyl alcohol, polyvinyl ether, ethyl cellulose, methyl cellulose, gum arabic, tragacanth, gelatin, shellac, hydroxypropyl cellulose, hydroxypropyl starch, and polyvinyl pyrrolidone. Examples of typical disintegrants include starch, agar, gelatin powder, crystalline cellulose, calcium carbonate, sodium hydrogencarbonate, calcium citrate, dextran, and pectin. Examples of appropriate lubricants include magnesium stearate, talc, polyethylene glycol, silica, and hardened vegetable oil. Examples of typical colorants include colorants which have been approved for addition to medicines.

Examples of acceptable corrigents include cacao powder, menthol, peppermint oil, refined borneol, and cinnamon. These tablets and granules may be coated with sugar, gelatin or the like as desired.

When preparing injections, a pH adjustor, a buffer, a stabilizer, an antiseptic and the like can be added. Subcutaneous, intramuscular or intravenous injections can be made in a conventional manner.

The stilbene compounds of the present invention can be formed into pharmaceutically acceptable acid-addition salts with inorganic acids such as hydrochloric acid, sulfuric acid and phosphoric acid and with organic acids such as oxalic acid, fumaric acid, maleic acid, malic acid, citric acid, tartaric acid and glutamic acid.

EXAMPLES

The present invention will be illustrated specifically by referring to the following Examples. However, the present invention is not limited to these Examples. Unless otherwise indicated herein, all parts, percents, ratios and the like are by weight. All amino acid abbreviations used herein are those commonly accepted.

Example 1

Synthesis of (Z)-1-(3-Amino-4-methoxyphenyl)-2-(3,4,5-trimethoxyphenyl)-ethene-glycineamide Step 1

Synthesis of (Z)-1-(3-Amino-4-methoxyphenyl)-2-(3,4,5-trimethoxyphenyl)-ethene-Fmoc-glycineamide Two grams (6.3 mmols) of (Z)-1-(3-amino-4-methoxyphenyl)-2-(3,4,5-trimethoxyphenyl)-ethene, 2.3 g of Fmoc-Gly and 11 g (25 mmols) of a BOP reagent were dissolved in 40 ml of N,N-dimethylformamide, and the mixture was heated at 60° C. for 2 hours. After the reaction mixture was cooled, a saturated aqueous solution of sodium hydrogencarbonate was added thereto. The resulting mixture was extracted three times with dichloromethane. The extract was dried over anhydrous sodium sulfate, and concentrated to dryness under reduced pressure. The product was purified through silica-gel column chromatography (mixture of ethyl acetate and hexane at a ratio by volume of 1:2) to give 1.63 of the final product in a yield of 43.5%.

$^1$H-NMR(CDCl$_3$) δ; 8.29(1H, s), 8.11(1H, s), 7.76(2H, d, J=7.5), 7.60(2H, d, J=7.5), 7.39(2H, t,J=7.2) 7.30(2H, m), 7.00(1H, dd, J=1.8, 8.7), 6.70(1H, d, J=8.7), 6.51(1H, d, J=12.3), 6.44(1H, d, J=12.3), 4.44(2H, d, J=6.6), 4.25(1H, m), 4.04(2H, 2H, br), 3.84(3H, s), 3.79(3H, s), 3.68(6H, s)

mass spectrum m/z: 594(M$^+$)

Step 2

Synthesis of (Z)-1-(3-Amino-4-methoxyphenyl)-2-(3,4,5-trimethoxyphenyl)-ethene-glycineamide (Z)-1-(3-Amino-4-methoxyphenyl)-2-(3,4,5-trimethoxyphenyl)-ethene-Fmoc-glycineamide (1.08 g, 1.82 mmols) was dissolved in 20 ml of methanol, and 1.0 ml (2.0 mmols) of a 2-N sodium hydroxide aqueous solution was added thereto. The mixture was stirred for 3 hours. A saturated solution of sodium hydrogencarbonate was added thereto, and the mixture was extracted three times with dichloromethane. The extract was dried over anhydrous sodium sulfate, and concentrated to dryness under reduced pressure. The product was purified using a silica-gel plate (mixture of 5-% methanol and dichloromethane) to produce 479 mg of the final product in a yield of 70.7%.

$^1$H-NMR(CDCl$_3$) δ; 9.61(1H, brs), 8.36(1H, d, J=1.8), 7.00(1H, dd, J=1.8, 8.4), 6.72(1H, d, J=8.4), 6.51(2H, s), 6.53(1H, d, J=12.0), 6.42(1H, d, J=12.0), 3.87(3H, s), 3.83 (3H, s), 3.68(6H, s)

mass spectrum m/z: 373(MH$^+$); high-resolution mass spectrum, calculated—373.1763, found—373.1751

Example 2

Synthesis of (Z)-1-(3-Amino-4-methoxyphenyl)-2-(3,4,5-trimethoxyphenyl)-ethene-L-alanineamide Step 1

Synthesis of (Z)-1-(3-Amino-4-methoxyphenyl)-2-(3,4,5-trimethoxyphenyl)-ethene-Fmoc-alanineamide (Z)-1-(3-Amino-4-methoxyphenyl)-2-(3,4,5-trimethoxyphenyl)-ethene (2.2 g, 6.9 mmols), 2.7 g (8.3 mmols) of Fmoc-L-Ala and 12.1 g (27.6 mmols) of a BOP reagent were dissolved in 22 ml of N,N-dimethylformamide, and the mixture was heated at 60° C. for 4 hours. After the reaction mixture was cooled, a saturated aqueous solution of sodium hydrogencarbonate was added thereto, and the resulting mixture was extracted three times with dichloromethane. The extract was dried over anhydrous sodium sulfate, and concentrated to dryness under reduced pressure. The product was purified through silica-gel column chromatography (mixture of ethyl acetate and hexane at a ratio of 1:2) to produce 1.79 g of the final product in a yield of 41.4%.

$^1$H-NMR(CDCl$_1$) δ; 8.32(1H, d, J=1.8), 8.19(1H, brs), 7.76(2H, d, J=7.2), 7.59(2H, d, J=7.2), 7.39(2H, t, J=6.9), 7.32(2H, m), 7.01(1H, dd, J=1.8, 8.7), 6.69(1H, d, J=8.4), 6.52(2H, s), 6.51(1H, d, J=12.0), 6.44(1H, d, J=12.0), 5.35 (1H, brs), 4.42(3H, br), 4.24(1H, m), 3.84(3H, s), 3.79(3H, s), 3.69(6H, s), 1.48(3H, d, J=6.9)

mass spectrum m/z: 608(M$^+$)

Step 2

Synthesis of (Z)-1-(3-Amino-4-methoxyphenyl)-2-(3,4,5-trimethoxyphenyl)-ethene-L-alanineamide One gram (1.6 mmols) of (Z)-1-(3-amino-4-methoxyphenyl)-2-(3,4,5-trimethoxyphenyl)-ethene-Fmoc-L-alanineamide was dissolved in 10 ml of methanol, and 0.9 ml (1.76 mmols) of an aqueous solution of 2-N sodium hydroxide were added thereto. The mixture was stirred for 3 hours. A saturated aqueous solution of sodium chloride was added thereto, and the resulting mixture was extracted three times with dichloromethane. The extract was dried over anhydrous sodium sulfate, and concentrated to dryness under reduced pressure. The product was purified using a silica-gel plate (mixture of 5-% by volume methanol and dichloromethane) to produce 543 mg of the final compound in a yield of 87.9%.

$^1$H-NMR(CDCl$_3$) δ; 9.72(1H, brs), 8.39(1H, d, J=2.1), 6.99(1H, dd, J=2.1, 8.4), 6.71(1H, d, J=8.4), 6.52 (1H, d, J=12.3), 6.52(2H, s), 6.42(1H, d, J=12.3), 3.86(3H, s), 3.83(3H, s), 3.68(6H, s), 3.64(1H, m), 1.43(3H, d, J=7.2)

mass spectrum m/z: 387(MH$^+$); high-resolution mass spectrum, calculated—387.1920, found—387.1922

Example 3

Synthesis of (Z)-1-(3-Amino-4-methoxyphenyl)-2-(3,4,5-trimethoxyphenyl)-ethene-L-leucineamide Step 1

Synthesis of (Z)-1-(3-Amino-4-methoxyphenyl)-2-(3,4,5-trimethoxyphenyl)-ethene-Fmoc-L-leucineamide (Z)-1-(3-Amino-4-methoxyphenyl)-2-(3,4,5-trimethoxyphenyl)-ethene (1.92 g, 6.1 mmols), 2.58 g (7.3 mmols) of Fmoc-L-Leu, 1.5 g (7.3 mmols) of DCC and 1.1 g (7.3 mmols) of HOBtH$_2$O were dissolved in 40 ml of N,N-dimethylformamide, and the mixture was reacted at room temperature for 12 hours. The reaction mixture was diluted with ethyl acetate, then filtered and concentrated. The product was purified through silica-gel column chromatography (mixture of ethyl acetate and hexane at a ratio by volume of 1:2) to produce 3.05 g of the final product in a yield of 76.9%.

$^1$H-NMR(CDCl$_3$) δ; 8.32(1H, d, J=2.1), 8.19(1H, s), 7.75(2H, d, J=7.5), 7.58(2H, d, J=7.5), 7.39(2H, t,J=6.9), 7.29(2H, m), 7.00(1H, dd, J=2.1, 8.4), 6.69(1H, d, J=8.4), 6.51(2H, s), 6.50(1H, d, J=12.3), 6.43(1H, d, J=12.3), 5.29 (1H, brs), 4.43(2H, d, J=6.9), 4.23(1H, t, J=6.9), 3.83(3H, s), 3.79(3H, s), 3.68(6H, s), 1.75(2H, br), 11.55(1H, br), 0.95 (6H, br)

mass spectrum m/z: 650(M$^+$)

Step 2

Synthesis of (Z)-1-(3-Amino-4-methoxyphenyl)-2-(3,4,5-trimethoxyphenyl)-ethene-L-leucineamide One gram (1.54 mmols) of (Z)-1-(3-amino-4-methoxyphenyl)-2-(3,4,5-trimethoxyphenyl) ethene-Fmoc-L-leucine was dissolved in 10 ml of methanol and 10 ml of dichloromethane, and 0.9 ml (1.7 mmols) of an aqueous solution of 2-N sodium hydroxide were added thereto. The mixture was stirred for 3 hours. A saturated aqueous solution of sodium chloride was added thereto, and the resulting mixture was extracted three times with dichloromethane. The extract was dried over anhydrous sodium sulfate, and concentrated to dryness under reduced pressure. The product was purified using a silica-gel column (mixture of 10-% by volume methanol and dichloromethane) to produce 560 mg of the final compound in a yield of 84.9%.

$^1$H-NMR(CDCl$_3$) δ; 9.78(1H, brs), 8.41(1H, d, J=1.8), 6.99(1H, dd, J=1.81, 8.4), 6.70(1H, d, J=8.4), 6.52(1H, d, J=12.3), 6.52(2H, s), 6.42(1H, d, J=8.4), 3.87(3H, s), 3.83 (3H, s), 3.68(6H, s), 3.51(1H, m), 1.80(2H, m), 1.42(1H, m), 0.98(6H, t, J=6.6)

mass spectrum m/z: 429 (MH$^+$); high-resolution mass spectrum, calculated—429.2389, found—429.2391

Example 4

Synthesis of (Z)-1-(3-Amino-4-methoxyphenyl)-2-(3,4,5-trimethoxyphenyl)-ethene-L-serineamide Step 1

Synthesis of (Z)-1-(3-Amino-4-methoxyphenyl)-2-(3,4,5-trimethoxyphenyl)-ethene-Fmoc-L-serineamide (Z)-1-(3-Amino-4-methoxyphenyl)-2-(3,4,5-trimethoxyphenyl)-ethene (1.5 g, 4.76 mmols), 2.1 g (5.7 mmols) of Fmoc-L-Ser(Ac), 1.2 g (5.7 mmols) of DCC and 0.87 g (5.7 mmols) of HOBt.H$_2$O were dissolved in 30 ml of N,N-dimethylformamide, and the mixture was reacted at room temperature for 5 hours. The reaction mixture was diluted with ethyl acetate, then filtered and concentrated. The product was purified through silica-gel column chromatography (mixture of ethyl acetate and hexane at a ratio by volume of 1:2) to produce 1.96 g of the final product in a yield of 61.8%.

$^1$H-NMR(CDCl$_3$) δ; 8.38(1H, br), 8.30(1H, d, J=1.8), 7.76(2H, d, J=7.8), 7.59(2H, d, J=7.8), 7.40(2H, t,J=7.2), 7.32(2H, m), 7.03(1H, dd, J=1.8, 8.7), 6.71(1H, d, J=8.7), 6.51(2H, s), 6.51(1H, d, J=12.3), 6.45(1H, d, J=12.3), 5.53 (1H, brs), 4.62(1H, br), 4.45(2H, d, J=6.9), 4.25(1H, m), 3.83(3H, s), 3.80(3H, s), 3.69(6H, s), 2.65(2H, d, J=9.3), 2.1(3H, s)

mass spectrum m/z: 666(M$^+$)

Step 2

Synthesis of (Z)-1-(3-Amino-4-methoxyphenyl)-2-(3,4,5-trimethoxyphenyl)-ethene-L-serineamide (Z)-1-(3-Amino-4-methoxyphenyl)-2-(3,4,5-trimethoxyphenyl)-ethene-Fmoc-L-serineamide (1.04 g, 1.56 mmols) was dissolved in 10 ml of methanol and 10 ml of dichloromethane, and 1.7 ml (3.4 mmols) of an aqueous solution of 2-N sodium hydroxide were added thereto. The mixture was stirred at room temperature for 24 hours. A saturated aqueous solution of sodium chloride was added thereto, and the resulting mixture was extracted three times with dichloromethane. The extract was dried over anhydrous sodium sulfate, and concentrated to dryness under reduced pressure. The product was purified using a silica-gel plate (mixture of 5-% by volume methanol and dichloromethane) to produce 315 mg of the final compound in a yield of 50.2%.

$^1$H-NMR(CDCl$_3$) δ; 9.77(1H, brs), 8.34(1H, d, J=2.1), 7.01(1H, dd, J=2.1, 8.7), 6.73(1H, d, J=8.7), 6.52(2H, s), 6.51(1H, d, J=12.3), 6.43(1H, d, J=12.3), 3.98(1H, dd, J=4.8, 11.1), 3.87(3H, s), 3.84(3H, s), 3.79(1H, dd, J=5.4, 11.1), 3.69(6H, s), 3.59(1H, dd, J=5.1, 5.4)

mass spectrum m/z: 403 (MH$^+$); high-resolution mass spectrum, calculated—403.1896, found—403.1862

Example 5

Synthesis of (Z)-1-(3-Amino-4-methoxyphenyl)-2-(3,4,5-trimethoxyphenyl)-ethene-L-threonineamide Step 1

Synthesis of (Z)-1-(3-Amino-4-methoxyphenyl)-2-(3,4,5-trimethoxyphenyl)-ethene-Fmoc-L-threonine(Ac)amide (Z)-1-(3-Amino-4-methoxyphenyl)-2-(3,4,5-trimethoxyphenyl)-ethene (1.5 g, 4.76 mmols), 2.2 g (5.7 mmols) of Fmoc-L-Ser(Ac), 1.2 g (5.7 mmols) of DCC and 0.87 g (5.7 mmols) of HOBt.H$_2$O were dissolved in 30 ml of N,N-dimethylformamide, and the mixture was reacted at room temperature for 6 hours. The reaction mixture was diluted with 50 ml of ethyl acetate, then filtered and concentrated. The product was purified through silica-gel column chromatography (mixture of ethyl acetate and hexane at a ratio by volume of 1:2) to give 2.97 g of the final product in a yield of 91%.

$^1$H-NMR(CDCl$_3$) δ; 8.36(1H, brs), 8.29(1H, d, J=2.4), 7.77(2H, m), 7.61(2H, m), 7.28–7.44(4H, m), 7.02(1H, dd, J=2.1, 8.7), 6.72(1H, d, J=8.7), 6.51(2H, s), 6.51(1H, d, J=12.0), 6.45(1H, d, J=12.0), 5.72(1H, m), 5.40(1H, m), 4.48(2H, m), 4.25(1H, m), 3.83(3H, s), 3.82(3H, s), 3.69 (6H, s), 2.08(3H, s), 1.24(3H, m)

mass spectrum m/z: 680(M$^+$)

Step 2

Synthesis of (Z)-1-(3-Amino-4-methoxyphenyl)-2-(3,4,5-trimethoxyphenyl )ethene-L-threonineamide One gram (1.47 mmols) of (Z)-1-(3-amino-4-methoxyphenyl)-2-(3,4,5-trimethoxyphenyl)-ethene-Fmoc-L-threonineamide(Ac)amide was dissolved in 20 ml of dioxane, and 1.76 ml (3.5 mmols) of an aqueous solution of 2-N sodium hydroxide were added thereto. The mixture was stirred for 24 hours. A saturated aqueous solution of sodium chloride was added thereto, and the resulting mixture was extracted three times with dichloromethane. The extract was dried over anhydrous sodium sulfate, and concentrated to dryness under reduced pressure. The product was purified using a silica-gel plate (mixture of 7.5-% methanol and dichloromethane) to produce 448 mg of the final compound in a yield of 73.4%.

$^1$H-NMR(CDCl$_3$) δ; 9.86(1H, brs), 8.37(1H, d, J=2.1), 7.01(1H, dd, J=2.1, 8.7), 6.72(1H, d, J=8.7), 6.52(2H, s), 6.52(1H, d, J=12.0), 6.43(1H, d, J=12.0), 4.42(1H, m), 3.87(3H, s), 3.84(3H, s), 3.69(6H, s), 3.38(1H, m), 1.25(3H, d, J=6.3)

mass spectrum m/z: 417(MH$^+$); high-resolution mass spectrum, calculated—417.2026, found—417.2050

Example 6

Synthesis of (E)-3-(3-Amino-4-methoxyphenyl)-2-(3,4,5-trimethoxyphenyl)-prop-2-enenitrile-glycineamide Hydrochloride Step 1

Synthesis of (E)-3-(3-Amino-4-methoxyphenyl)-2-(3,4,5-trimethoxyphenyl)-prop-2-enenitrile-Boc-glycineamide Seven-hundred milligrams (1.86 mmols) of (E)-3-(3-amino-4-methoxyphenyl)-2-(3,4,5-trimethoxyphenyl)-prop-2-enenitrile hydrochloride, 478 mg of WSCI, 375 mg of HOBt.H$_2$O and 486 mg of Boc-Gly were dissolved in 100 ml of N,N-dimethylformamide, and 0.35 ml of triethylamine were added thereto. The mixture was reacted at 50° C. for 3.5 hours. Seven-hundred milliliters of water were added thereto, and the resulting mixture was extracted with ethyl acetate. Subsequently, the ethyl acetate layer was washed three times with water, dried over anhydrous sodium sulfate, and concentrated under reduced pressure. The product was purified using a silica-gel column (eluent, ether), and then dissolved in a small amount of dichloromethane. Diethyl ether was added thereto for crystallization to obtain 1.71 mmols of the final product in a yield of 92%.

$^1$H-NMR(CDCl$_3$) δ; 1.481(s,9H), 3.759(s,6H), 3.855(s, 3H), 3.883(s,3H), 3.901(d,J=5.7 Hz), 5.1(br,1H), 6.603(s, 2H), 6.696(d,J=8.5 Hz, 1H), 6.892(d–d,J=1.8 Hz, 8.5 Hz,1H), 7.245(s,1H), 8.295(br.s,1H), 8.333(d,J=1.8 Hz,1H)

mass spectrum m/z: 497(M$^+$)

Step 2

Synthesis of (E)-3-(3-Amino-4-methoxyphenyl)-2-(3,4,5-trimethoxyphenyl)-prop-2-enenitrile-glycineamide Eight-hundred milligrams of (E)-3-(3-amino-4-methoxyphenyl)-2-(3,4,5-trimethoxyphenyl)-prop-2-enenitrile-Boc-glycineamide were dissolved in 3 ml of dichloromethane, and 3 ml of a solution of 4-M hydrochloric acid and dioxane were added thereto. The mixture was reacted at room temperature for 2 hours. Thirty milliliters of diethyl ether were added thereto, and the resulting mixture was filtered. The thus-obtained powder was hot-washed with a mixture of chloroform, isopropanol and toluene at a ratio by of 6:8:20 to produce 483 mg (1.11 mmols) of the final compound in a yield of 65%.

$^1$H-NMR(CD$_3$OD) δ; 3.735(s,6H), 3.807(br,2H), 3.812(s, 3H), 3.888(s,3H), 6.662(s,2H), 6.978(d,J=8.6 Hz, 1H), 7.102(d-d,J=2.1 Hz, 8.6 Hz,1H), 7.346(s,1H), 8.018(d, J=2.1 Hz, 1H)

high-resolution mass spectrum, calculated—398.1716, found—398.1723

Example 7

Synthesis of (E)-3-(3-Amino-4-methoxyphenyl)-2-(3,4,5-trimethoxyphenyl)-prop-2-enenitrile-L-ornithineamide Dihydrochloride Step 1

Synthesis of (E)-3-(3-Amino-4-methoxyphenyl)-2-(3,4,5-trimethoxyphenyl)-prop-2-enenitrile-Boc-L-ornithineamide Seven-hundred milligrams (1.86 mmols) of (E)-3-(3-amino-4-methoxyphenyl)-2-(3,4,5-trimethoxyphenyl)-prop-2-enenitrile hydrochloride, 463 mg of WSCI, 463 mg of HOBt.H$_2$O and 767 mg of Boc$_2$-L-Orn were dissolved in 70 ml of N,N-dimethylformamide, and 0.35 ml of triethylamine were added thereto. The mixture was reacted at 50° C. for 41 hours. Four-hundred milliliters of water were added thereto, and the resulting mixture was extracted with diethyl ether. Subsequently, the diethyl ether layer was washed three times with water, dried over anhydrous sodium sulfate, and concentrated under reduced pressure. The product was purified using a silica-gel column (eluent, diethyl ether), and then dissolved in a small amount of dichloromethane. Diethyl ether was added thereto for crystallization to produce 737 mg (1.13 mmols) of the final product in a yield of 61%.

$^1$H-NMR(CDCl$_3$) δ; 1.432(s,9H), 1.451(s,9H), 1.5(m, 2H), 1.65(m,1H), 1.9(m,1H), 3.2(m,2H), 3.764(s,6H), 3.857 (s, 3H),3.875(s,3H), 4.2(br,1H), 4.8(br,1H), 5.1(br,1H), 6.600(s,2H), 6.704(d,J=8.6 Hz,1H), 6.901 (d–d, J=2.1 Hz,8.6 Hz,1H), 7.236(s,1H), 8.266(d,J=2.1 Hz,1H), 8.329 (br.s,1H)

mass spectrum m/z: 654(M$^+$)

Step 2

Synthesis of (E)-3-(3-Amino-4-methoxyphenyl)-2-(3,4,5-trimethoxyphenyl)-prop-2-enenitrile-L-ornithineamide Hydrochloride (E)-3-(3Amino-4-methoxyphenyl)-2-(3,4,5-trimethoxyphenyl)-prop-2-enenitrile-Boc-L-ornithineamide (730 mg, 1.11 mmols) was dissolved in 5 ml of dichloromethane, and 5 ml of a solution of 4-M hydrochloric acid and dioxane were added thereto. The mixture was reacted at room temperature for 1 hour. One-hundred milliliters of diethyl ether were added thereto, and the resulting mixture was filtered. The thus-obtained powder was recrystallized from a mixture of methanol and ethyl acetate at a ratio by volume of 1:1 to produce 286 mg (0.542 mmols) of the final compound in a yield of 48%.

$^1$H-NMR(CDCl$_3$) δ; 1.7(m,2H), 1.9(m,2H), 2.973(d,J= 6.3 Hz,1H), 3.003(d,J=6.3 Hz,1H), 3.768(s,6H), 3.820(s, 3H), 3.898(s,3H), 4.176(t,J=6.3 Hz,1H), 6.675(s,2H), 7.014 (d,J=8.5 Hz, 1H), 7.173(d–d,J=2.0 Hz,8.5 Hz,1H), 7.368(s, 1H), 7.801(d, J=2.0 Hz,1H)

high-resolution mass spectrum, calculated—455.2288, found—455.2300

Example 8

Synthesis of (E)-3-(3-Amino-4-methoxyphenyl)-2-(3,4,5-trimethoxyphenyl)-prop-2-enenitrile-L-phenylaranineamide Hydrochloride Step 1

Synthesis of (E)-3-(3-Amino-4-methoxyphenyl)-2-(3,4,5-trimethoxyphenyl)-prop-2-enenitrile-Boc-L-phenylaranineamide (E)-3-(3-Amino-4-methoxyphenyl)-2-(3,4,5-trimethoxyphenyl)-prop-2-enenitrile hydrochloride (998 mg, 2.65 mmols), 1,290 mg of a BOP reagent and 777 mg of Boc-L-Phe were dissolved in 50 ml of acetonitrile, and 0.8 ml of triethylamine were added thereto. The mixture was reacted at room temperature for 18 hours and at 50° C. for 20 hours. One-hundred milliliters of water were added thereto, and the resulting mixture was extracted with ethyl acetate. Subsequently, the extract was dried over anhydrous sodium sulfate, and concentrated under reduced pressure. The product was purified using a silica-gel column (eluent, dichloromethane), and then dissolved in a small amount of dichloromethane. Diethyl ether and hexane (in an amount of 20 ml and 30 ml, respectively) were added thereto for crystallization to produce 1,082 mg (1.84 mmols) of the final product in a yield of 69%.

$^1$H-NMR(CDCl$_3$) δ; 1.426(s,9H), 3.12(br.t,2H), 3.744(s, 3H), 3.766(s,6H), 3.888(s,3H), 4.4(br,1H), 5.1(br,1H), 6.613 (s,2H), 6.639(d,J=8.8 Hz,1H), 6.875(d-d, J=2.1 Hz,8.8 Hz,1H), 7.18–7.36(m,5H), 8.030(br.s,1H), 8.345(d,J=2.1 Hz,1H)

FAB mass spectrum m/z: 587(M$^+$)

Step 2

Synthesis of (E)-3-(3-Amino-4-methoxyphenyl)-2-(3,4,5-trimethoxyphenyl)-prop-2-enenitrile-L-phenylalanineamide Hydrochloride (E)-3-(3-Amino-4-methoxyphenyl)-2-(3,4,5-trimethoxyphenyl)-prop-2-enenitrile-Boc-L-phenylalanineamide (1,082 mg, 1.11 mmols) was dissolved in 10 ml of dichloromethane, and 5 ml of a solution of 4-M hydrochloric acid and dioxane were added thereto. The mixture was reacted at room temperature for 1 hour. One-hundred milliliters of diethyl ether were added thereto, and the resulting mixture was filtered. The thus-obtained powder was recrystallized from a mixture of chloroform, methanol and ethyl acetate at a ratio of 4:1:4 to produce 450 mg (0.859 mmols) of the final compound in a yield of 77%.

$^1$H-NMR(CD$_3$OD) δ; 3.106(d,J=7.3 Hz,1H), 3.119(d,J=7.3 Hz,1H), 4.312(t,J=7.3 Hz,1H), 3.751(s,6H), 3.792(s, 3H), 3.819(s,3H), 6.672(s,2H), 6.936(d, J=8.7 Hz,1H), 7.173(d-d,J=2.2 Hz,8.7 Hz,1H), 7.2(m,2H), 7.3(m,3H), 7.339(s,1H), 7.878(d,J=2.2 Hz,1H)

high-resolution mass spectrum, calculated—488.2186, found—488.2162

Example 9

Synthesis of (E)-3-(3-Amino-4-methoxyphenyl)-2-(3,4,5-trimethoxyphenyl)-prop-2-enenitrile-L-prolineamide Hydrochloride Step 1

Synthesis of (E)-3-(3-Amino-4-methoxyphenyl)-2-(3,4,5-trimethoxyphenyl)-prop-2-enenitrile-Boc-L-prolineamide (E)-3-(3-Amino-4-methoxyphenyl)-2-(3,4,5-trimethoxyphenyl)-prop-2-enenitrile hydrochloride (998 mg, 2.65 mmols), 1,300 mg of a BOP reagent and 605 mg of Boc-L-Pro were dissolved in 50 ml of acetonitrile, and 0.8 ml of triethylamine were added thereto. The mixture was reacted at room temperature for 18 hours and at 50° C. for 20 hours. One-hundred milliliters of water and a small amount of sodium hydrogencarbonate were added thereto, and the resulting mixture was extracted with ethyl acetate. Subsequently, the extract was dried over anhydrous sodium sulfate, and concentrated under reduced pressure. The product was purified using a silica-gel column (eluent, dichloromethane), and then concentrated to produce 1,310 mg (2.44 mmols) of the final product in a yield of 92%.

$^1$H-NMR(CDCl$_3$) δ; 1.4–1.5(br,9H), 1.9(br,2H), 2.1–2.3 (br,1H), 2.3–2.5(br,1H), 3.3–3.5(br,2H), 3.753(s,6H), 3.838 (s,3H), 3.876(s,3H), 4.2–4.5(br,1H), 6.609(s,2H), 6.677(d, J=8.4 Hz,1H), 6.871(m,1H), 7.238(s,1H), 8.39(br.s,1H), 9.2 (br,1H)

FAB mass spectrum m/z: 537(M$^+$)

Step 2

Synthesis of (E)-3-(3-Amino-4-methoxyphenyl)-2-(3,4,5-trimethoxyphenyl)-prop-2-enenitrile-L-prolineamide Hydrochloride (E)-3-(3-Amino-4-methoxyphenyl)-2-(3,4,5-trimethoxyphenyl)-prop-2-enenitrile-Boc-L-prolineamide (1,250 mg, 2.33 mmols) was dissolved in 10 ml of dichloromethane, and 5 ml of a solution of 4-M hydrochloric acid and dioxane were added thereto. The mixture was reacted at room temperature for 1 hour. One-hundred milliliters of diethyl ether were added thereto, and the mixture was filtered. The resulting powder was purified through medium-pressure liquid chromatography (ODS, mixture of water and acetonitrile at a ratio of 70:30). The product was recrystallized three times with a mixture of chloroform and ethyl acetate at a ratio by volume of 1:10 to produce 465 mg (0.980 mmols) of the final product in a yield of 42%.

$^1$H-NMR(CDCl$_3$) δ; 2.0(m,3H), 2.4(m,1H), 3.4(m,2H), 3.745(s,6H), 3.805(s,3H), 3.895(s,3H), 4.45(m,1H), 6.660 (s,2H), 6.997(d,J=8.6 Hz,1H), 7.143(d–d,J=2.1 Hz,8.6 Hz,1H), 7.349(s,1H), 7.839(d,J=2.1 Hz,1H)

high-resolution mass spectrum, calculated—438.2029, found—438.2033

Example 10

Synthesis of (E)-3-(3-Amino-4-methoxyphenyl)-2-(3,4,5-trimethoxyphenyl)-prop-2-enenitrile-L-alanineamide Hydrochloride Step 1

Synthesis of (E)-3-(3-Amino-4-methoxyphenyl)-2-(3,4,5-trimethoxyphenyl)-prop-2-enenitrile-Boc-L-alanineamide (E)-3-(3-Amino-4-methoxyphenyl)-2-(3,4,5-trimethoxyphenyl)-prop-2-enenitrile hydrochloride (1,053 mg, 2.65 mmols), 1,300 mg of a BOP reagent and 554 mg of Boc-L-Ala were dissolved in 50 ml of acetonitrile, and 0.8 ml of triethylamine were added thereto. The mixture was reacted at 60° C. for 17 hours. One-hundred milliliters of water and a small amount (about 10 g) of sodium hydrogencarbonate were added thereto, and the resulting mixture was extracted with ethyl acetate. The extract was washed with a saturated aqueous solution of sodium chloride, then dried over anhydrous sodium sulfate, and concentrated under reduced pressure. The product was purified using a silica-gel column (eluent, mixture of dichloromethane and ethyl acetate at a ratio of 20:1), and then concentrated to produce 1,085 mg (2.12 mmols) of the final product in a yield of 80%.

Step 2

Synthesis of (E)-3-(3-Amino-4-methoxyphenyl)-2-(3,4,5-trimethoxyphenyl)-prop-2-enenitrile-L-alanineamide Hydrochloride One-thousand milligrams (1.95 mmols) of (E)-3-(3-amino-4-methoxyphenyl)-2-(3,4,5-trimethoxyphenyl)-prop-2-enenitrile-Boc-L-aranineamide were dissolved in 10 ml of dichloromethane, and 5 ml of a solution of 4-M hydrochloric acid and dioxane were added thereto. The mixture was reacted at room temperature for 1 hour. One-hundred milliliters of diethyl ether were added thereto, and the mixture was filtered. The resulting powder was recrystallized twice from a mixture of chloroform, methanol and ethyl acetate at a ratio by volume of 20:2:30. The thus-obtained powder was purified through medium-pressure liquid chromatography (ODS, mixture of water and acetonitrile at a ratio by volume of 75:25). The powder purified was dissolved in a small amount of methanol, and diethyl ether was added thereto. The precipitate was collected by filtration to produce 280 mg (0.625 mmols) of the final product in a yield of 32%.

$^1$H-NMR(CD$_3$OD) δ; 1.503(d,J=7.0 Hz,3H), 3.736(s,6H), 3.808(s,3H), 3.888(s,3H), 4.129(q,J=7.0 Hz, 1H), 6.662(s, 2H), 6.985(d,J=8.6 Hz,1H), 7.122(d–d,J=2.3 Hz,8.6 Hz,1H), 7.345 (s,1H), 7.900(d,J=2.3 Hz,1H)

high-resolution mass spectrum, calculated—412.1873, found—412.1873

Example 11

Synthesis of (E)-3-(3-Amino-4-methoxyphenyl)-2-(3,4,5-trimethoxyphenyl)-prop-2-enenitrile-L-threonineamide Hydrochloride Step 1

Synthesis of (E)-3-(3-Amino-4-methoxyphenyl)-2-(3,4,5-trimethoxyphenyl)-prop-2-enenitrile-Boc-L-threonineamide One-thousand milligrams (2.65 mmols) of (E)-3-(3-amino-4-methoxyphenyl)-2-(3,4,5-trimethoxyphenyl)-prop-2-enenitrile hydrochloride, 1,300 mg of a BOP reagent and 880 mg of Boc-L-Thr (OtBu) were dissolved in 50 ml of acetonitrile, and 0.8 ml of triethylamine were added thereto. The mixture was reacted at 60° C. for 21 hours. One-hundred milliliters of water and a small amount of sodium hydrogencarbonate were added thereto, and the resulting mixture was extracted with ethyl acetate. The extract was washed with a saturated aqueous solution of sodium chloride, then dried over anhydrous sodium sulfate, and concentrated under reduced pressure. The product was purified using a silica-gel column (eluent, mixture of ethyl acetate and hexane at a ratio by volume of 5:1), and then concentrated to produce 870 mg (1.46 mmols) of the final product in a yield of 55%.

$^1$H-NMR(CD$_3$OD) δ; 1.044(d,J=6.0 Hz,3H), 1.315(s,9H), 1.463(s,9H), 3.760(s,6H), 3.844(s,3H), 3.887(s,3H), 4.15 (br.m,1H), 4.22(br,1H), 5.64(br.d,1H), 6.617(s,2H), 6.857(d, J=8.5 Hz,1H), 6.897(d–d,J=2.2 Hz,8.5 Hz,1H), 7.228(s,1H), 8.404(d,J=2.2 Hz,1H), 9.3(br.s,1H)

FAB mass spectrum: 597(M$^+$)

Step 2

Synthesis of (E)-3-(3-Amino-4-methoxyphenyl)-2-(3,4,5-trimethoxyphenyl)-prop-2-enenitrile-L-threonineamide Hydrochloride (E)-3-(3-Amino-4-methoxyphenyl)-2-(3,4,5-trimethoxyphenyl)-prop-2-enenitrile-Boc-L-threonineamide (810 mg, 1.95 mmols) were dissolved in 10 ml of dichloromethane, and 5 ml of a solution of 4-M hydrochloric acid and dioxane were added thereto. The mixture was reacted at 60° C. for 3 hours. One-hundred milliliters of diethyl ether were added thereto, and the mixture was filtered. The resulting powder was purified twice through medium-pressure liquid chromatography (ODS, mixture of water and acetonitrile at a ratio of 75:25), and was dissolved in a small amount of methanol. A mixture of acetonitrile and ethyl acetate was added thereto, and the precipitate was collected by filtration to obtain 290 mg (0.607 mmols) of the final product in a yield of 31%.

$^1$H-NMR(CD$_3$OD) δ; 1.240(d,J=6.3 Hz,3H), 3.9(1H), 3.739(s,6H), 3.810(s,3H), 3.892(s,3H), 4.012(m,1H), 6.658 (s,2H), 6.996(d,J=8.5 Hz,1H), 7.133 (d–d,J=2.2 Hz, 8.5 Hz,1H), 7.350(s,1H), 7.923(d,J=2.2 Hz,1H)

high-resolution mass spectrum, calculated—442.1978, found—442.1973

Example 12

Synthesis of (E)-3-(3-Amino-4-methoxyphenyl)-2-(3,4,5-trimethoxyphenyl)-prop-2-enenitrile-L-lysineamide Dihydrochloride Step 1

Synthesis of (E)-3-(3-Amino-4-methoxyphenyl)-2-(3,4,5-trimethoxyphenyl)-prop-2-enenitrile-Boc-L-lysineamide One-thousand milligrams (2.65 mmols) of (E)-3-(3-amino-4-methoxyphenyl)-2-(3,4,5-trimethoxyphenyl)-prop-2-enenitrile hydrochloride and 1,462 mg of Boc$_2$-L-LysOSu were dissolved in 50 ml of acetonitrile, and 0.8 ml of triethylamine were added thereto. The mixture was reacted at 60° C. for 20 hours. Six-hundred milligrams of HOBt and 1,300 mg of a BOP reagent were added thereto, and the mixture was further reacted at 60° C. for 21 hours. One-hundred milliliters of water and a small amount of sodium hydrogencarbonate were added thereto, and the resulting mixture was extracted with ethyl acetate. The extract was washed with a saturated aqueous solution of sodium chloride, then dried over anhydrous sodium sulfate, and concentrated under reduced pressure. The product was purified using a silica-gel column (eluent, dichloromethane), and then concentrated to produce 1,170 mg (1.74 mmols) of the final product in a yield of 66%.

$^1$H-NMR(CDCl$_3$) δ; 1.438(s,9H), 1.450(s,9H), 1.4–1.5 (br,4H), 1.7(br,1H), 1.9(br,1H), 3.1(br,2H), 3.756(s,6H), 3.852(s,3H), 3.874(s,3H), 4.2(br,1H), 4.7(br,1H), 5.2(br, 1H), 6.604(s,2H), 6.685(d,J=8.7 Hz,1H), 6.884(d–d,J=2.2 Hz,8.7 Hz,1H), 7.231(s,1H), 8.348(br,1H)

FAB mass spectrum: 668(M$^+$)

Step 2

Synthesis of (E)-3-(3-Amino-4-methoxyphenyl)-2-(3,4,5-trimethoxyphenyl)-prop-2-enenitrile-L-lysineamide Dihydrochloride (E)-3-(3-Amino-4-methoxyphenyl)-2-(3,4,5-trimethoxyphenyl)-prop-2-enenitrile-Boc-L-lysineamide (1,1000 mg, 1.64 mmols) were dissolved in 10 ml of dichloromethane, and 5 ml of a solution of 4-M hydrochloric acid and dioxane were added thereto. The mixture was reacted at 60° C. for 3 hours. One-hundred milliliters of diethyl ether were added thereto, and the mixture was filtered. The resulting powder was purified through medium-pressure liquid chromatography (ODS, mixture of water and acetonitrile at a ratio by volume of from 95:5 to 85:15), and was dissolved in a small amount of methanol (10 ml). A mixture of acetonitrile and ethyl acetate was added thereto, and the precipitate obtained was collected by filtration to produce 300 mg (0.554 mmols) of the final product in a yield of 34%.

$^1$H-NMR (CD$_3$OD) δ; 1.4(m,2H), 1.7(m,2H), 1.9(m,2H), 2.95(m,2H), 3.756(s,6H), 3.811(s,3H), 3.896(s,3H), 4.131(t, J=6.3), 6.667(s,2H), 7.010(d,J=8.9 Hz, 1H), 7.164(d–d,J= 2.3 Hz, 8.9 Hz,1H), 7.361(s,1H), 7.834(d,J=2.3 Hz,1H)

high-resolution mass spectrum, calculated—469.2451, found—469.2454

Example 13

Synthesis of (E)-3-(3-Amino-4-methoxyphenyl)-2-(3,4,5-trimethoxyphenyl)-prop-2-enenitrile-L-serineamide Hydrochloride Step 1

Synthesis of (E)-3-(3-Amino-4-methoxyphenyl)-2-(3,4,5-trimethoxyphenyl)-prop-2-enenitrile-Fmoc-L-serineamide (E)-3-(3-Amino-4-methoxyphenyl)-2-(3,4,5-trimethoxyphenyl)-prop-2-enenitrile hydrochloride (1,007 mg, 2.65 mmols), 1,105 mg of Fmoc-L-Ser(OtBu)OH, 1,370 mg of a BOP reagent and 618 mg of HOBt.H$_2$O were dissolved in 50 ml of acetonitrile, and 0.8 ml of triethylamine were added thereto. The mixture was reacted at 60° C. for 42 hours. One-hundred milliliters of water and a small amount of sodium hydrogencarbonate were added thereto, and the resulting mixture was extracted with ethyl acetate. The extract was washed with a saturated aqueous solution of sodium chloride, then dried over anhydrous sodium sulfate, and concentrated under reduced pressure. The product was purified using a silica-gel column (eluent, mixture of ethyl acetate and hexane at a ratio of 2:3), and then concentrated to produce 1,486 mg (2.14 mmols) of the final product in a yield of 81%.

¹H-NMR(CDCl₃) δ; 1.241(s,9H), 3.243(t,J=8.5 Hz,1H), 3.760(s,6H), 3.832(s,3H), 3.874(s,3H), 4.247(m,1H), 4.33 (br,1H), 4.42(m,2H), 5.8(br,1H), 6.617(s,2H), 6.704(d,J=8.8Hz,1H), 6.904(d–d,J=2.2 Hz,8.8 Hz,1H), 7.252(s,1H), 7.32(m,2H), 7.407(t,J=7.5 Hz,2H), 7.612(d,J=7.5 Hz,2H), 7.772(d,J=7.2 Hz,2H), 8.406(d,J=2.2 Hz), 9.0(br.s,1H)

FAB mass spectrum: 705(M⁺)

Step 2

Synthesis of (E)-3-(3-Amino-4-methoxyphenyl)-2-(3,4,5-trimethoxyphenyl)-prop-2-enenitrile-L-serineamide Hydrochloride (E)-3-(3-Amino-4-methoxyphenyl)-2-(3,4,5-trimethoxyphenyl)-prop-2-enenitrile-Fmoc-L-serineamide (1,430 mg, 2.07 mmols) were dissolved in 5 ml of chloroform and 2 ml of piperidine. The reaction was conducted for 1 hour, and the product was then purified using a silica-gel column (eluent, mixture of ethyl acetate and dichloromethane at a ratio by volume of 1:1). The thus-purified product was concentrated to dryness under reduced pressure, and then dissolved in 10 ml of a solution of 4-M hydrochloric acid and dioxane. The resulting mixture was reacted at 70°C. for 1 hour. One-hundred milliliters of diethyl ether were added thereto, and the resulting precipitate was collected by filtration. The thus-obtained powder was purified through medium-pressure liquid chromatography (ODS, mixture of water and acetonitrile at a ratio by volume of from 75:25), and was heat-dissolved in a mixture of chloroform and methanol at a ratio of 5:1 to produce 460 mg (0.992 mmols) of the final product in a yield of 48%.

¹H-NMR(CD₃OD) δ; 3.737(s,6H), 3.813(s,3H), 3.892(s, 3H), 3.9(m,2H), 4.123(d–d,J=5.1 Hz,6.3 Hz,1H), 6.662(s, 2H), 6.981(d,J=8.5 Hz,1H), 7.109(d–d,J=2.2 Hz,8.5 Hz,1H), 7.344(s,1H), 7.998(d,J=2.2 Hz,1H)

high-resolution mass spectrum, calculated—428.1822, found—428.1806

Example 14

Synthesis of (E)-3-(3-Amino-4-methoxyphenyl)-2-(3,4,5-trimethoxyphenyl)-prop-2-enenitrile-L-aspartylamide Hydrochloride Step 1

Synthesis of (E)-3-(3-Amino-4-methoxyphenyl)-2-(3,4,5-trimethoxyphenyl)-prop-2-enenitrile-Fmoc-L-aspartylamide Nine-hundred milligrams (2.65 mmols) of (E)-3-(3-amino-4-methoxyphenyl)-2-(3,4,5-trimethoxyphenyl)-prop-2-enenitrile, 1,400 mg of Fmoc-L-Asp(OBn), 1,300 mg of a BOP reagent and 660 mg of HOBt.H₂O were dissolved in 50 ml of acetonitrile, and 0.5 ml of triethylamine were added thereto. The mixture was reacted at room temperature for 86 hours. One-hundred milliliters of water and a small amount of sodium hydrogencarbonate were added thereto, and the resulting mixture was extracted with ethyl acetate. The extract was washed with a saturated aqueous solution of sodium chloride, then dried over anhydrous sodium sulfate, and concentrated under reduced pressure. The product was purified using a silica-gel column (eluent, mixture of ethyl acetate and dichloromethane at a ratio by volume of 1:10), and then concentrated to give 1,319 mg (1.80 mmols) of the final product in a yield of 68%.

¹H-NMR(CDCl₃) δ; 2.76(br.d–d,1H), 3.15(br.d,1H), 3.747(s,9H), 3.869(s,3H), 4.231(t,J=7.0 Hz,1H), 4.457(m, 2H), 4.72(br,1H), 5.133(d,J=12.3 Hz,1H), 5.206(d,J=12.3 Hz,1H), 6.607(s,2H), 6.662(d,J=9.0 Hz,1H), 6.896(d–d,J= 2.1 Hz,9.0 Hz,1H), 7.20–7.45(m,4H), 7.342(s,1H), 7.58 (br.d,2H), 7.762(d–d,J=2.5 Hz, 7.3 Hz,2H), 8.327(d,J=2.1 Hz), 8.7(br.s,1H)

FAB mass spectrum: 767(M⁺)

Step 2

Synthesis of (E)-3-(3-Amino-4-methoxyphenyl)-2-(3,4,5-trimethoxyphenyl)-prop-2-enenitrile-L-aspartylamide Hydrochloride (E)-3-(3-Amino-4-methoxyphenyl)-2-(3,4,5-trimethoxyphenyl)-prop-2-enenitrile-Fmoc-L-aspartylamine (1,210 mg, 1.65 mmols) were dissolved in 30 ml of dioxane, and 2 ml of an aqueous solution of 2-M sodium hydroxide were added thereto. The mixture was reacted at room temperature for 1 hour, and 100 ml of ether were added thereto. The resulting precipitate was collected by filtration. This precipitate was dissolved again in 30 ml of dioxane, and 0.5 ml of an aqueous solution of 2-M sodium hydroxide and 1.5 ml of water were added thereto. The mixture was reacted at room temperature for 1 hour. Subsequently, 100 ml of ether were added thereto, and the resulting precipitate was collected by filtration. The thus-filtered product was purified in small portions through medium-pressure liquid chromatography (ODS, mixture of water, methanol and 12-N hydrochloric acid at a ratio by volume of 75:25:0.3). The fraction having a purity of 90% or more was concentrated, and dissolved in 200 ml of a mixture of 2-M hydrochloric acid and methanol at a ratio by volume of 10:1. The solution was neutralized with a 2-M NaOH aqueous solution, and allowed to stand for 40 minutes. The resulting precipitate was collected by filtration. The thus-filtered product was dissolved in a small amount of methanol containing 0.3 ml of a solution of 4-M hydrochloric acid and dioxane. Ethyl acetate was added thereto, and the resulting precipitate was collected by filtration to produce 292 mg (0.594 mmols) in a yield of 36%.

¹H-NMR(CD₃OD) δ; 3.08(m, 2H), 3.752(s, 6H), 3.812(s, 3H), 3.868(s, 3H), 4.256(t, J=5.4 Hz, 1H), 6.646(s, 2H), 6.948(d, J=8.6 Hz, 1H), 7.086(d–d, J=2.0 Hz, 8.6 Hz, 1H), 7.330(s, 1H), 7.821(d, J=2.0 Hz, 1H)

high-resolution mass spectrum, calculated—456.1771, found—456.1775

Example 15

Synthesis of (E)-3-(3-Amino-4-methoxyphenyl)-2-(3,4,5-trimethoxyphenyl)-prop-2-enenitrile-L-glutamylamide Hydrochloride Step 1

Synthesis of (E)-3-(3-Amino-4-methoxyphenyl)-2-(3,4,5-trimethoxyphenyl)-prop-2-enenitrile-Fmoc-L-glutamyl (OBn)amide Hydrochloride Nine-hundred milligrams (2.65 mmols) of (E)-3-(3-amino-4-methoxyphenyl)-2-(3,4,5-trimethoxyphenyl)-prop-2-enenitrile, 1,500 mg of Fmoc-L-Glu(OBn), 1,300 mg of a BOP reagent and 643 mg of HOBt.H₂O were dissolved in 50 ml of acetonitrile, and 0.5 ml of triethylamine were added thereto. The mixture was reacted at room temperature for 64 hours. One-hundred milliliters of water and a small amount of sodium hydrogencarbonate were added thereto, and the resulting mixture was extracted with dichloromethane. The extract was washed with a saturated aqueous solution of sodium chloride, then dried over anhydrous sodium sulfate, and concentrated under reduced pressure. The product was purified using a silica-gel column (eluent, dichloromethane), and then concentrated to produce 1,950 mg (2.55 mmols) of the final product in a yield of 97%.

¹H-NMR(CDCl₃) δ; 1.9–2.1(br.m, 1H), 2.1–2.3(br.m, 1H), 2.4–2.7(br.m, 2H), 3.745(s, 6H), 3.788(s, 3H), 3.868(s,

3H), 3.85–3.95(m, 1H), 4.207(t, J=6.9 Hz, 1H), 4.408(d, J=6.9 Hz, 2H), 5.137(s, 2H), 5.6–5.7(br.s, 1H), 6.603(s, 2H), 6.675(d, J=8.7 Hz, 1H), 6.899(d–d, J=2.0 Hz, 8.7 Hz, 1H), 7.2–7.4(m, 10H), 7.577(d, J=7.5 Hz, 2H), 7.754(d, J=7.5 Hz, 2H), 8.320(m, 2H)

FAB mass spectrum: 781($M^+$)

Step 2

Synthesis of (E)-3-(3-Amino-4-methoxyphenyl)-2-(3,4,5-trimethoxyphenyl)-prop-2-enenitrile-L-glutamylamide Hydrochloride (E)-3-(3-Amino-4-methoxyphenyl)-2-(3,4,5-trimethoxyphenyl)-prop-2-enenitrile-Fmoc-L-glutamyl (OBn)amine (1,940 mg, 2.55 mmols) were dissolved in 50 ml of dioxane, and 3.7 ml of an aqueous solution of 2-M sodium hydroxide were added thereto. The mixture was reacted at room temperature for 1 hour, and 100 ml of diethyl ether were added thereto. The resulting precipitate was collected by filtration. This precipitate was dissolved again in 30 ml of dioxane, and 0.5 ml of 2-M sodium hydroxide and 1.5 ml of water were added thereto. The mixture was reacted at room temperature for 1 hour. Subsequently, 20 ml of methanol were added to the reaction solution, and the mixture was poured into 250 ml of diethyl ether. The resulting precipitate was collected by filtration. The thus-filtered product was purified in small portions through medium-pressure liquid chromatography (ODS, mixture of water, acetonitrile and 12-N hydrochloric acid at a ratio by volume of 75:25:0.3). The thus-purified product was concentrated without being dried. When the amount of the solution reached approximately 50 ml, the solution was added to a mixture of ethyl acetate and diethyl ether at a ratio by volume of 1:1, and precipitated. After the supernatant was discarded, 110 ml of acetonitrile and 350 ml of diethyl ether were added to the residue in this order. The resulting precipitate was filtered, washed with ether, and dried under reduced pressure to obtain 436 mg (0.838 mmols) in a yield of 33%.

$^1$H-NMR(CD$_3$OD) δ; 2.120(q, J=7.0 Hz, 2H), 2.468(m, 2H), 3.735(s, 6H), 3.808(s, 3H), 3.888(s, 3H), 4.131(t, J=6.3 Hz, 1H), 6.658(s, 2H), 6.995(d, J=8.6 Hz, 1H), 7.143(d–d, J=2.2 Hz, 8.6 Hz, 1H), 7.349(s, 1H), 7.861(d, J=2.2 Hz, 1H)

high-resolution mass spectrum, calculated—470.1927, found—470.1914

Example 16

Evaluation of Cytotoxicity:

Mouse P388 leukemia cells were used as cancer cells, and a RPMI-1640 medium containing 5-μM 2-mercaptoethanol and 10% fetal bovine serum was used in the incubation. The above-mentioned cells were inoculated on a 96-well microplate in an amount of 1×10$^4$ cells/50 μl/well, and an aqueous solution of a test compound (4 μg/ml) was added thereto in an amount of 25 μl/well. The mixture was incubated at 37° C. for 2 days. Then, the number of live cells were counted using the MTT method, and a dose-response curve was then prepared. A 50% growth inhibitory concentration (IC$_{50}$) given for the test compound was calculated according to the dose-response curve. The IC$_{50}$ values obtained of the compounds are tabulated below. Minimum doses which exert acute death immediately after injection are also shown in the table.

Example 17

Test for the Pharmaceutical Effect on Mice:

Colon 26 which had been cloned subcutaneously in mice was cut with scissors, and implanted subcutaneously in mice by means of a trocar. One week later, the tumors were measured using calipers, and the volumes of the tumors were calculated. The mice were grouped (each group consisting of 3 mice). The test compound was dissolved with dimethylsulfoxide and diluted with 5% by volume Tween 80/saline. A 0.2 ml of the solution was injected intravenously once a day on Day 7, Day 11 and Day 15 after the implantation. On Day 21 after the implantation, the volumes of the tumors were measured. The volume of the tumor and the tumor growth inhibition rate (I.R.) were calculated using the following expressions.

$$\text{Volume of Tumor} = \frac{(\text{Short Diameter})^2 \times (\text{Long Diameter})}{2}$$

$$I.R.\ (\%) = \frac{1 - (\text{Average Tumor Volume of Agent-Administered Group})}{(\text{Average Tumor Volume of Control Group})} \times 100$$

| Compound Name | Formula | in vitro IC$_{50}$ (ng/ml) | in vivo [a] I.R. (%) | Toxic Dose (mg/kg) [b] |
|---|---|---|---|---|
| (Z)-1-(3-amino-4-methoxyphenyl)-2-(3,4,5-trimethoxyphenyl)-ethene-L-glycine amide | 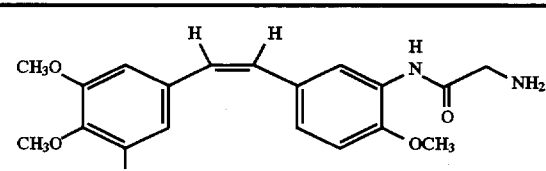 | 2.0 | 33.3 (40 mg/kg) | 80 |
| (Z)-1-(3-amino-4-methoxyphenyl)-2-(3,4,5-trimethoxyphenyl)-ethene-L-alanine amide | 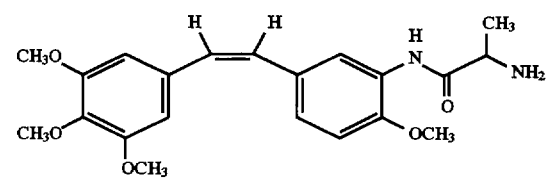 | 2.0 | 51.9 (40 mg/kg) | 80 |

-continued

| Compound Name | Formula | in vitro IC$_{50}$ (ng/ml) | in vivo [a] I.R. (%) | Toxic Dose (mg/kg) [b] |
|---|---|---|---|---|
| (Z)-1-(3-amino-4-methoxy phenyl)-2-(3,4,5-trimethoxy phenyl)-ethene-L-leucine amide | | 6.0 | 50.9 (40 mg/kg) | 40 |
| (Z)-1-(3-amino-4-methoxy phenyl)-2-(3,4,5-trimethoxy phenyl)-ethene-L-serine amide | | 4.0 | 72.9 (80 mg/kg) | 160 |
| (Z)-1-(3-amino-4-methoxy phenyl)-2-(3,4,5-trimethoxy phenyl)-ethene-L-threonine amide | | 6.0 | 62.2 (80 mg/kg) | 160 |
| (E)-3-(3-amino-4-methoxy phenyl)-2-(3,4,5-trimethoxy phenyl)-prop-ene-nitrile-L-glycine amide | | 3.0 | 85.7 (20 mg/kg) | 40 |
| (E)-3-(3-amino-4-methoxy phenyl)-2-(3,4,5-trimethxy phenyl)-prop-ene-nitrile-L-alanine amide | | 0.5 | 71.0 (20 mg/kg) | 80 |
| (E)-3-(3-amino-4-methoxy phenyl)-2-(3,4,5-trimethxy phenyl)-prop-ene-nitrile-L-serine amide | | 2.0 | 75.0 (80 mg/kg) | 160 |
| (E)-3-(3-amino-4-methoxy phenyl)-2-(3,4,5-trimethxy phenyl)-prop-ene-nitrile-L-threonine amide | | 6.0 | 67.0 (40 mg/kg) | 320 |
| (E)-3-(3-amino-4-methoxy phenyl)-2-(3,4,5-trimethxy phenyl)-prop-ene-nitrile-L-phenylalanine amide | | 5.0 | 76.7 (40 mg/kg) | 80 |

-continued

| Compound Name | Formula | in vitro IC$_{50}$ (ng/ml) | in vivo [a] I.R. (%) | Toxic Dose (mg/kg) [b] |
|---|---|---|---|---|
| (E)-3-(3-amino-4-methoxy phenyl)-2-(3,4,5-trimethxy phenyl)-prop-ene-nitrile-L-proline amide | | 200 | 68.9 (40 mg/kg) | 40 |
| (E)-3-(3-amino-4-methoxy phenyl)-2-(3,4,5-trimethxy phenyl)-prop-ene-nitrile-L-ornithine amide | | 50.0 | 48.9 (10 mg/kg) | N.D. |
| (E)-3-(3-amino-4-methoxy phenyl)-2-(3,4,5-trimethxy phenyl)-prop-ene-nitrile-L-lysine amide | | 13.0 | 33.8 (10 mg/kg) | 20 |
| (E)-3-(3-amino-4-methoxy phenyl)-2-(3,4,5-trimethxy phenyl)-prop-ene-nitrile-L-aspartyl amide | | 2.0 | 1.7 (10 mg/kg) | 40 |
| (E)-3-(3-amino-4-methoxy phenyl)-2-(3,4,5-trimethxy phenyl)-prop-ene-nitrile-L-glutamyl amide | | 4.0 | 77.0 (40 mg/kg) | 80 |

[a] Administered intravenously once a day on day 7, day 11 and day 15.
[b] A minimum dose which show death immediately after injection.

While the invention has been described in detail and in reference to specific embodiments thereof, it will be apparent that various changes can made without departing from the scope of the present invention.

What is claimed is:

1. A stilbene compound represented by formula (I)

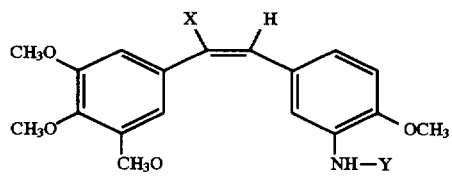

wherein X represents a hydrogen atom or a nitrile group, and Y represents an amino acid acyl group.

2. The stilbene compound of claim 1, wherein X is a hydrogen atom.

3. The stilbene compound of claim 1, wherein X is a nitrile group.

4. The stilbene compound of claim 1 or 2, wherein Y is L-α-amino acid acyl group.

5. The stilbene compound of claim 4, wherein Y is a threonine or serine residue.

6. A pharmaceutical composition comprising a carcinostatically effective amount of a stilbene compound or a pharmaceutically acceptable salt thereof of claim 1 and a pharmaceutically acceptable excipient, diluent or carrier.

7. A method for treating cancer in a subject comprising administering to said subject in need of such treatment a carcinostatically effective amount of a compound of claim 1.

* * * * *